United States Patent [19]
Dieken et al.

[11] Patent Number: 5,663,532
[45] Date of Patent: Sep. 2, 1997

[54] ERGONOMETRIC STETHOSCOPE CHESTPIECE

[75] Inventors: Alan P. Dieken, Oakdale; Edward J. Moe, St. Paul, both of Minn.; Joy A. Packard; Thomas J. Packard, both of Somerset, Wis.; Thomas W. Reeder, Asheville, N.C.; Thomas A. Turgeon, Fridley, Minn.

[73] Assignee: Minnesota Mining and Manufacturing Company, St. Paul, Minn.

[21] Appl. No.: 563,187

[22] Filed: Nov. 27, 1995

[51] Int. Cl.$^6$ .................................................. A61B 7/02
[52] U.S. Cl. .................................................. 181/131; 181/137
[58] Field of Search .................................. 181/131, 137; 381/67; D24/134

[56] References Cited

U.S. PATENT DOCUMENTS

| | | |
|---|---|---|
| D. 185,178 | 5/1959 | Spears, Jr. . |
| D. 205,171 | 6/1966 | Littmann . |
| D. 213,257 | 1/1969 | Littmann . |
| D. 214,002 | 4/1969 | Machlup et al. . |
| D. 227,890 | 7/1973 | Loughridge et al. . |

(List continued on next page.)

FOREIGN PATENT DOCUMENTS

| 43 42 768 | 6/1994 | Germany . |
|---|---|---|

OTHER PUBLICATIONS

Brochure entitled "Littmann Classis II and Pediatric and Infant Stethoscope", dated Jan. 5, 1994, (1 page).

Brochure entitled, "The Allen Series", by Newport Instruments, Inc. (1983), (5 pages).

Brochure entitled, "Adgram", vol. 8, Issue 5, by American Diagnostic Corporation, Sep.–Oct. 1994, (1 page). Note the Master Adscope™ 600.

Brochure entitled, "Anesthesia Specialties", by Buffalo Medical Specialties MFG. Inc. (1983), (17 pages).

Brochure entitled, "Series 22 Stethoscope", Series 12 Stethoscope, and Price List dated Mar. 1, 1980, by Newport Instruments, Inc., (4 pages).

*Primary Examiner*—Khanh Dang
*Attorney, Agent, or Firm*—Gary L. Griswold; Walter N. Kirn; Karl H. Bartingale

[57] ABSTRACT

An ergonometric chestpiece for a stethoscope adapted to receive auscultatory sounds from a body and adapted to be coupled to an earpiece for a user. The chestpiece is adapted to be grasped by a thumb and at least one finger of the user. The chestpiece has a bottom surface which is generally planar and is adapted to be placed near the body for receiving the auscultatory sounds. The chestpiece has an upper portion opposite the bottom surface. The upper portion has a raised center portion defining left and right indented gripping surfaces which form recesses defined by the left and right indented gripping surfaces and by a surface generally parallel to but opposite the bottom surface. The left and right indented gripping surfaces are adapted to receive the thumb and at least one finger of the user, respectively. The indented gripping surfaces have indented impressions adapted to be easily, securely and comfortably grasped by the thumb and fingers of the user. The indented gripping surfaces are each further defined by a protruding edge on the top surface of the raised center portion which prevent the fingers of the user from slipping upward and thus prevent the chestpiece from slipping out of the user's hand. The raised center portion form a physical stop to prevent the thumb and fingers of the user from slipping forward and contacting the body when the thumb and the at least one finger grasp the raised center of the upper portion. The left and right walls may be concave. The ergonometric chestpiece may be generally circular and the left and right walls are cylindrically concave around axes generally orthogonal to the bottom surface. The top surface of the raised center portion may be sloped with respect to the bottom surface, the top surface being closer to the bottom surface at the front of the chestpiece than at the rear of the chestpiece.

15 Claims, 3 Drawing Sheets

U.S. PATENT DOCUMENTS

| | | |
|---|---|---|
| D. 323,394 | 1/1992 | Casto et al. . |
| D. 337,381 | 7/1993 | Dufresne et al. . |
| D. 338,269 | 8/1993 | Dufresne et al. . |
| D. 353,196 | 12/1994 | Savage et al. . |
| 3,108,652 | 10/1963 | Littmann . |
| 3,275,099 | 9/1966 | Speelman . |
| 3,288,246 | 11/1966 | Allen . |
| 3,339,667 | 9/1967 | Speelman . |
| 3,472,335 | 10/1969 | Allen . |
| 4,212,368 | 7/1980 | Allen .................................... 181/131 |
| 4,254,302 | 3/1981 | Walshe . |
| 4,440,258 | 4/1984 | Packard . |
| 4,475,619 | 10/1984 | Packard . |
| 4,569,413 | 2/1986 | Allen . |
| 4,852,684 | 8/1989 | Packard . |
| 4,913,259 | 4/1990 | Packard . |
| 4,928,786 | 5/1990 | Allen .................................... 181/137 |
| 4,995,473 | 2/1991 | Packard . |
| 5,204,500 | 4/1993 | Dufresne et al. . |
| 5,288,953 | 2/1994 | Peart . |
| 5,347,583 | 9/1994 | Dieken et al. ........................ 381/67 |
| 5,367,575 | 11/1994 | Dieken et al. . |

ERGONOMETRIC STETHOSCOPE CHESTPIECE

TECHNICAL FIELD

The present invention relates generally to stethoscopes and, more particularly, to chestpieces for stethoscopes, especially electronic stethoscopes having operational controls located on the chestpiece.

BACKGROUND ART

Stethoscopes have long been used by physicians to monitor auscultatory sounds. Typically stethoscopes have been comprised of a head or chestpiece, a sound transmission mechanism and an earpiece assembly. The chestpiece is adapted to be placed against the skin of a patient for gathering the auscultatory sounds. The sound transmission mechanism transmits the gathered sound to the earpiece where the physician may monitor the sound.

The chestpiece of conventional auditory stethoscopes are usually quite simple physically. They are usually round disk shapes sometimes dual sided, top and bottom with a diaphragm covering one side, to allow either side of the chestpiece to contact the skin of the patient for the gathering of auscultatory sounds in different frequency ranges.

Recently, the auditory sound gathering, transmission and delivery functions of stethoscopes have been supplemented or supplanted by electronic gathering or transmission.

The incorporation of electronic circuitry into the stethoscope has been a considerable design problem for the engineer. Typically, the electronic circuitry increases the physical size of the stethoscope package. Typically, either the size of the chestpiece is increased in size dramatically or an additional enclosure to house the electronics is located between the chestpiece and earpiece or both. In both of these cases, the resulting stethoscope is bulky, cumbersome to use and not easily storable between uses. The result, thus, is a stethoscope which is distinctly not ergonometric.

SUMMARY

The chestpiece has a raised center portion which is adapted to be grasped by the thumb and one or more fingers of the user. The top surface of raised center portion preferably is sloped downward from rear to front of chestpiece to form a surface which easily fits into the palm of the hand of the user.

The chestpiece further includes indented gripping surfaces that are adapted to easily, securely and comfortably engage the gripping appendages (thumb and one or more fingers) of the user. The indented gripping surfaces are defined by walls which are concave generally along one or more axis generally orthogonal to the bottom surface of chestpiece. The walls defining indented gripping surfaces are also preferably concave generally along an axis generally parallel to the bottom surface of the chestpiece to create an indented impression in the indented gripping surfaces into which the thumb and fingers of the user can securely and comfortably fit.

In addition, each of the indented gripping surfaces also include a protruding edge on the top surface of the raised center portion. The area formed by the indented gripping surfaces and the respective protruding edges define left and right recesses which are adapted to receive the thumb and at least one finger of the user.

In an alternative embodiment, to further increase the security of the indented gripping surfaces, the walls of the indented gripping surfaces may be roughened, textured, or have ridges formed thereon.

In another alternative embodiment, the chestpiece also includes at least one finger recess located on the top surface of the raised center portion.

BRIEF DESCRIPTION OF THE DRAWINGS

The foregoing advantages, construction and operation of the present invention will become more readily apparent from the following detailed description and accompanying drawings in which.

DETAILED DESCRIPTION

Figure 1:
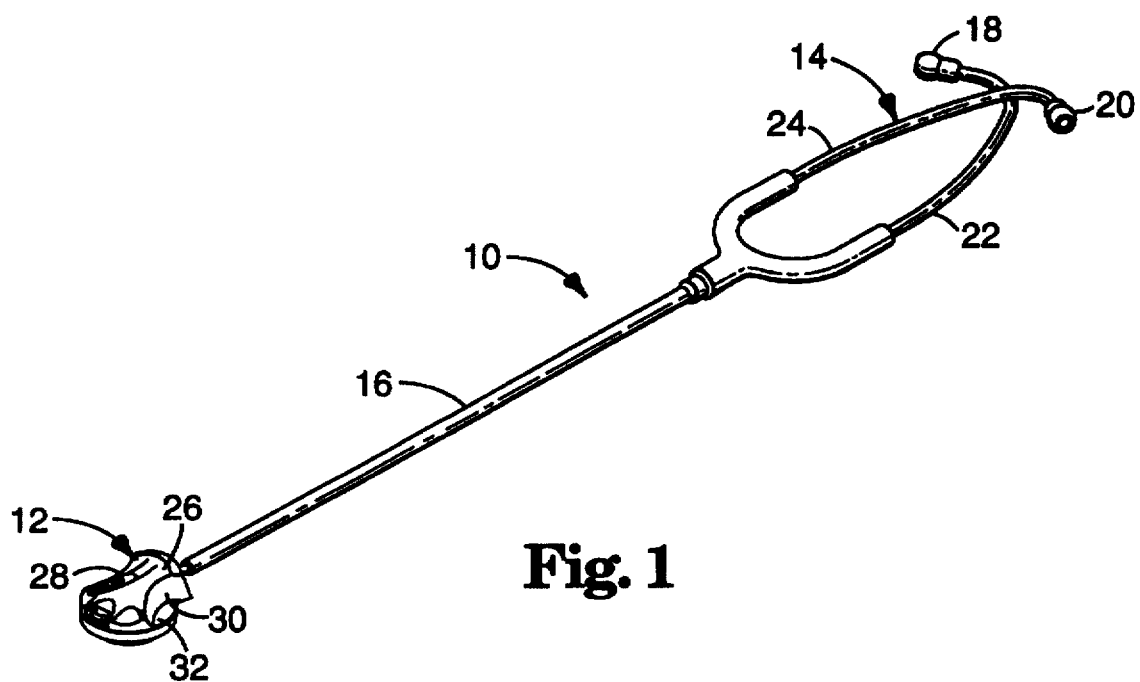
FIG. 1 is a top plan view illustrating a stethoscope incorporating the chestpiece according to one embodiment of the present invention.
Figure 2:
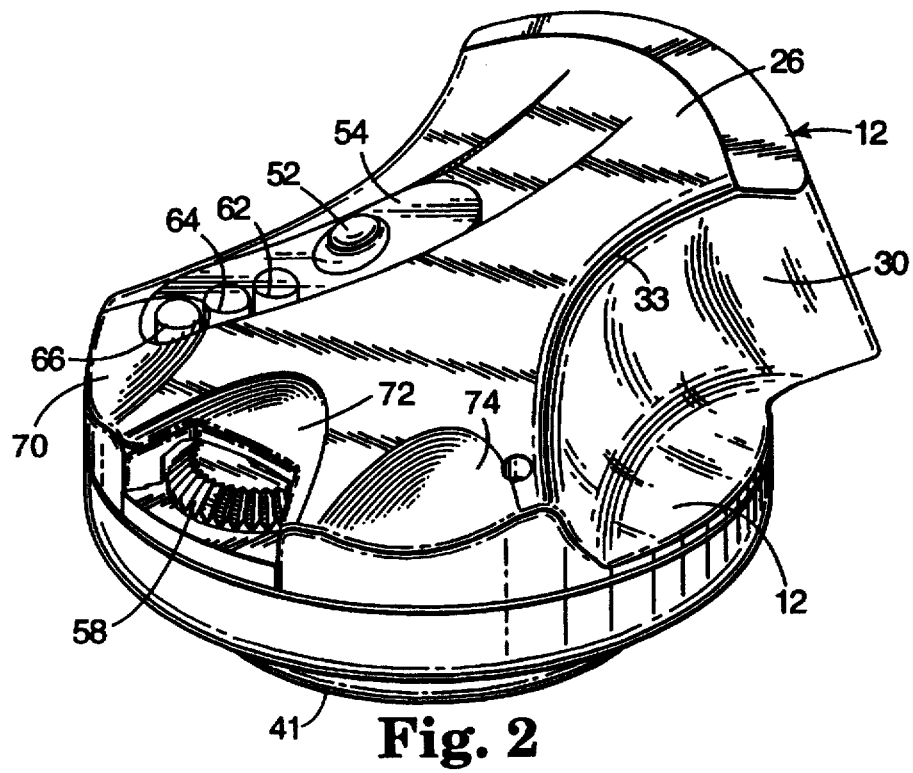
FIG. 2 is a perspective view of an illustrative embodiment of the chestpiece of the present invention.
Figure 3:
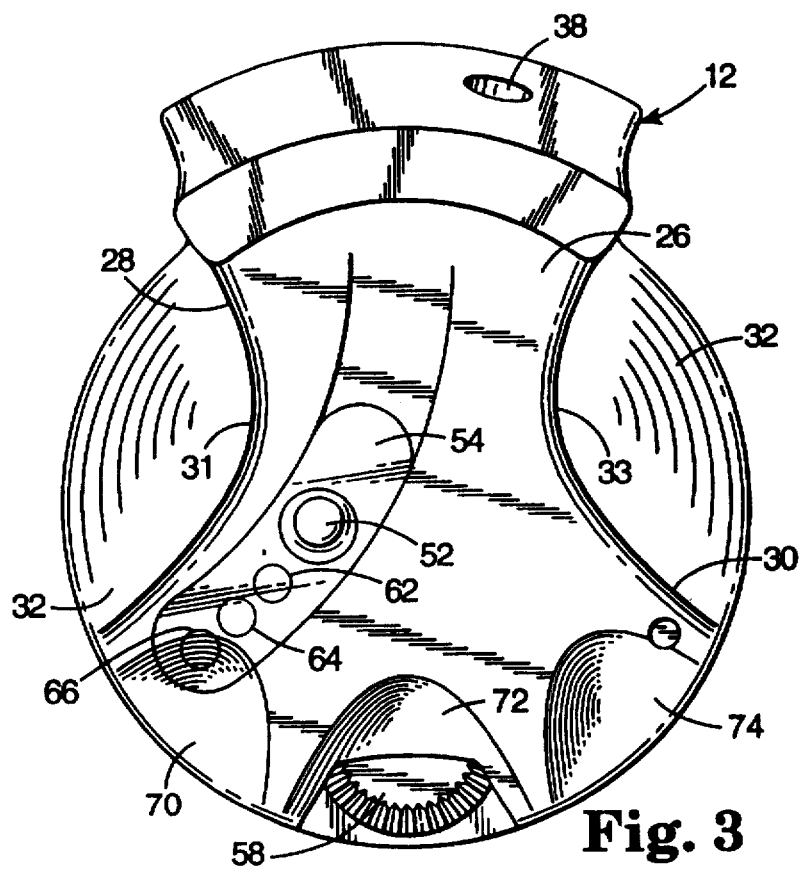
FIG. 3 top view of the illustrative embodiment of the chestpiece of the present invention.
Figure 4:
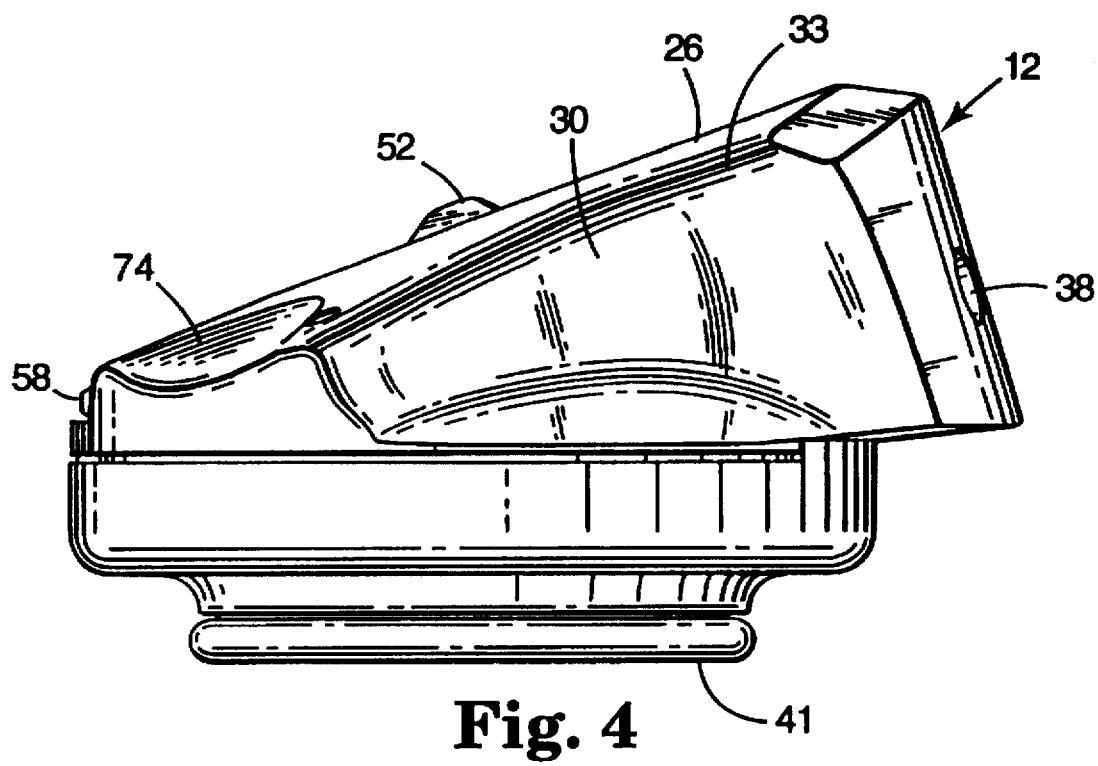
FIG. 4 is a side view of the illustrative embodiment of the chestpiece of the present invention.
Figure 5:
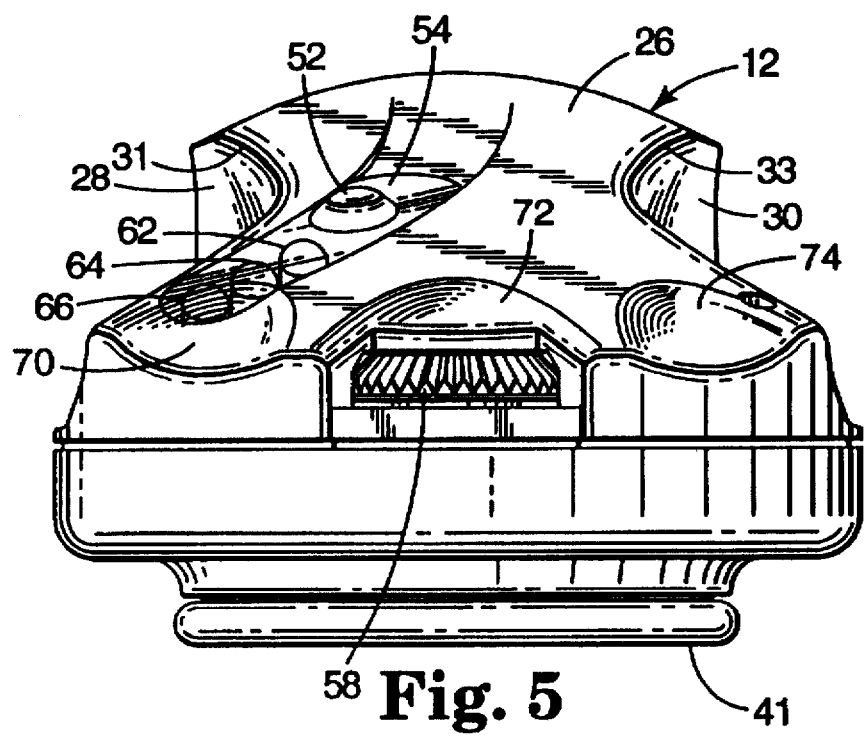
FIG. 5 is a front view of the illustrative embodiment of the chestpiece of the present invention.

The stethoscope 10 illustrated in FIG. 1 consists of a chestpiece 12, or stethoscope head, a headpiece 14 and a connecting tube 16. The headpiece 14 has two eartips 18 and 20 adapted to fit in the ear of a user, typically a physician or other medical professional. Tubes 22 and 24, generally acoustic tubes, couple eartips 18 and 20, respectively to connecting tube 16 which in turn is coupled to chestpiece 12.

The sound transmission system of stethoscope 10 may be entirely acoustic as is well known in the art. However, it is also contemplated that the sound transmission system of stethoscope 10 could also be electronic. In this situation, an acoustic to electronic transducer, a microphone, would be located along the acoustic sound transmission path, typically in or very near the chestpiece 12, and even more typically in the chestpiece 12 positioned in a shallow cone near the bottom surface (not shown in FIG. 1) of the chestpiece 12 so as to be near the source of auscultatory sounds. Electronic means would then typically amplify, or otherwise process, the electrical signal. The electrical signal may be transmitted electrically to an electrical acoustic transducer, a speaker or speakers, typically located nearer the earpieces 22 and 24 of the stethoscope 10. Of course, a stethoscope of a combination acoustic and electronic, or dual acoustic and electronic, is also contemplated. In one embodiment, the stethoscope is an electronic stethoscope of the type described in U.S. Patent Application filed on even date herewith, entitled "ELECTRONIC STETHOSCOPE WITH IDEALIZED BELL AND IDEALIZED DIAPHRAGM MODES", Ser. No. 08/563,186.

FIGS. 2, 3, 4, and 5 shows perspective, top left side and front views of the illustrative stethoscope chestpiece. The bottom surface 41 of the chestpiece 12 is adapted to be placed near the source of auscultatory sound, or, in a preferred embodiment, to contact the skin of the patient. Chestpiece 12 has a raised center portion 26 which is adapted to be grasped by the thumb and one of the fingers of the user, typically the thumb and middle finger. The top surface of raised center portion 26 preferably is sloped downward from rear to front of chestpiece 12 to form a surface which may be easily formed into the palm of the hand of the user. Thus, raised center portion 26 is higher, i.e., thicker, at the rear of the chestpiece 12 than at the front of the chestpiece 12.

Indented gripping surfaces 28 and 30 of the raised center portion 26 are adapted to easily, securely and comfortably engage the gripping appendages (thumb and one or more fingers) of the user. Indented gripping surfaces 28 and 30 are defined by walls which are arcuate about one or more axis generally orthogonal to the bottom surface of chestpiece 12 and further are defined by the surface 32 of the chestpiece 12 opposite the bottom surface. The walls defining indented gripping surfaces 28 and 30 are also preferably arcuate about an axis generally parallel to the bottom surface of the chestpiece 12 to create an indented impression in the indented gripping surfaces 28 and 30 into which the thumb and fingers of the user can securely and comfortably fit. In other words, the walls of the indented gripping surfaces 28 and 30 are concavely curved in two directions; from the front toward the back, and from the top toward the bottom. The walls of the resulting indented gripping surfaces 28 and 30 are thus formed with an impression indented inwards toward the center of the chestpiece. In this manner, the indented gripping surfaces are adapted to fit the curves of the user's gripping fingers.

In addition, each of the indented gripping surfaces 28 and 30 also include a protruding edge 31 and 33, respectively. The area formed by the indented impressions in the walls of indented gripping surfaces 28 and 30, the respective protruding edges 31 and 33 and surface 32 define left and right recesses which are adapted to receive the thumb and at least one finger of the user.

The indented impressions of the left and right recesses formed into raised center portion 26 allow indented gripping surfaces 28 and 30 and the associated protruding edges 31 and 33 allow comfortable placement and secure gripping of the chestpiece by the user. The protruding edges 31 and 33 on indented gripping surfaces 28 and 30 prevent the fingers or thumb of the user from slipping upward during use and eliminates the possibility that the chestpiece will slip out of the user's grip during use. In addition, the flared out portions of the left and right recesses form into raised center portion 26 allow gripping surfaces 28 and 30 to act as a physical stop which prevents the fingers or thumb of the user from sliding forward during use and eliminates the possibility of the fingers and/or thumb slipping off of the chestpiece 12. Any of these types of slippage could result in an interruption of the monitoring of auscultatory sounds and further could result in pain and/or embarrassment to the user and/or the patient. The protruding edges 31 and 33 facilitates the physical stop of the user's fingers slipping upward. The flaring out of the indented gripping surfaces to an angle outward of directly forward in the chestpiece facilitates the physical stop of the user's fingers forward. It is preferred that this angle be at least thirty degrees from straight forward and, still further preferably, this should be at least about forty-five degrees but, for comfort, substantially less than ninety degrees from straight forward on the chestpiece 12.

In addition, because the indented gripping surfaces 28 and 30 are indented inwards to fit the curve of the user's fingers, the user is provided with tactile feedback concerning the positioning of the chestpiece in the hand. This feedback allows the user to know, understand and adjust, if necessary, the positioning of the chestpiece in the hand without having to visually perceive the chestpiece.

In one preferred embodiment, the chestpiece 12 also includes at least one finger recess, such as recesses 70, 72, and 74. Finger recesses 70 and 74 provide rest positions for the user's index finger when it is not operating one of the operational controls 52 or 58. Finger recess 72 provides the user with tactile feedback concerning the location of the rotary switch 58, and can also be used as an alternative rest position. The tactile feedback provided by finger recesses 70, 72, and 74 help the user properly position the chestpiece in the hand and easily locate the operational controls without having to visually perceive the chestpiece.

To further increase the security of the indented gripping surfaces 28 and 30, the walls of the indented gripping surfaces may be roughened, textured, or have ridges formed thereon. The roughened surface may be regular or irregular. In the case of a regularly textured surface, the walls of the indented gripping surfaces 28 and 30 may be scored or impressed with a fish gill or knurled pattern, for example. By roughening or texturing the walls of the indented gripping surfaces 28 and 30, the security of the chestpiece in the hand is improved. In addition, the ability of the user to adequately grip the chestpiece is improved, thus reducing the likelihood of the chestpiece slipping out of the user's grip.

It is preferred that the ergonometric chestpiece 12 has a shape which is generally circular. Further, where the shape of chestpiece 12 is generally circular, the left and right walls formed by indented gripping surfaces 28 and 30 are preferred to be cylindrically concave around axes generally orthogonal to the bottom surface.

At least one operational control, in this embodiment a push-button switch 52, is positioned on the top surface of the raised center portion 26. Push-button switch 52 is positioned roughly in the middle of raised center portion 26 generally forward of indented gripping surfaces 28 and 30. In this position, push-button switch 52 is easily available to be manipulated by the index finger of the user when indented gripping surfaces 28 and 30 are grasped by the user's thumb and middle finger. Typical uses of push-button switch 52 are to turn power to the stethoscope 10 on, or select different modes of operation of the stethoscope, for example, by selecting a different frequency response of the stethoscope.

The push-button switch 52 is located in recess 54 on the top surface and of raised center portion 26. Mode indicators 62, 64, and 66 are also located within recess 54. Recess 54 itself is arcuate, skewing toward the outside edge of raised center portion 26 similar to the wall formed by indented gripping surface 28. In a preferred embodiment, the recess 54, push-button switch 52, and mode indicators 62, 64, and 66 are covered with a silicon resilient membrane that is semi-transparent to allow the user to view the status of the mode indicators 62, 64, and 66.

Rotary control 58 (potentiometer) is positioned in a recess near the front edge of raised center portion 26 and chestpiece 12. The rotary action of switch 58 is in a plane parallel to the plane of bottom surface 36. In an alternate preferred embodiment, the rotary action of switch 58 is in a plane perpendicular to the plane of bottom surface 36, wherein the plane is positioned from the back to the front of the stethoscope chestpiece. In a typical function, push-button switch 52 may be used to control power to the stethoscope and control the mode selection of the stethoscope, and rotary switch 58 may be used to control the volume of the stethoscope 10. Mode indicators 62, 64 and 66 indicate the current mode in which the stethoscope is operating. All of these controls are easily accessible to and easily manipulated by the index finger of the user. The resulting chestpiece is one which can easily and comfortably be used by both right and left handed users.

It shall be understood that different chestpieces differing with respect to the number, placement and form of the operational controls could be substituted for the specific embodiment shown without departing from the scope of the present invention.

Connecting tube 16 (not shown in FIGS. 2, 3, 4 and 5) is coupled to chestpiece 12 at the rear of chestpiece 12 at opening 38.

Thus, chestpiece 12 functions quite ergonometrically in use by the physician or other health care professional.

What is claimed is:

1. An ergonometric chestpiece for a stethoscope adapted to receive auscultatory sounds from a body and adapted to be coupled to an earpiece for a user, said chestpiece adapted to be grasped by a thumb and at least one finger of said user, comprising:

said chestpiece having a bottom surface which is generally planar adapted to be placed near said body for receiving said auscultatory sounds;

said chestpiece having an upper portion opposite said bottom surface;

said upper portion having a raised center portion defining left and right indented gripping surfaces forming recesses defined by said left and right indented gripping surfaces and by a surface opposite said bottom surface, said left and right indented gripping surfaces adapted to receive said thumb and said at least one finger of said user, respectively;

said raised center portion forming a physical stop for said thumb and said at least one finger from contacting said body when said thumb and said at least one finger grasp said raised center of said upper portion;

said indented gripping surfaces being defined by left and right walls, each having a concave surface arcuate about an axis generally normal to said bottom surface;

said indented gripping surfaces further having an indented impression arcuate about an axis generally parallel to said bottom surface; and said indented gripping surfaces each further having a protruding edge on a top surface of said raised center portion.

2. An ergonometric chestpiece as in claim 1 wherein the top surface of said raised center portion is sloped with respect to said bottom surface, said top surface being closer to said bottom surface at the front of said chestpiece than at the rear of said chestpiece.

3. An ergonometric chestpiece as in claim 1 which further comprises at least one operational control placed on said raised center portion in a position easily manipulated by an index finger of said user.

4. An ergonometric chestpiece as in claim 3 wherein at least one said operational control is mounted on the top surface of said raised center portion of said chestpiece.

5. An ergonometric chestpiece as in claim 4 wherein said at least one control is placed on the forward portion of said raised center portion of said chestpiece.

6. An ergonometric chestpiece as in claim 5 wherein said chestpiece is coupled to said earpiece at the rear of said chestpiece.

7. An ergonometric chestpiece as in claim 5 wherein said chestpiece has a plurality of controls all located on the top surface of said raised center portion, said plurality of controls are ergonometrically positioned for manipulation by an index finger of said user.

8. An ergonometric chestpiece as in claim 7 wherein the plurality of controls are ergonometrically positioned for use with a right hand or a left hand of the user.

9. An ergonometric chestpiece as in claim 7 wherein each of said plurality of controls is recessed.

10. An ergonometric chestpiece as in claim 9 which further comprises a rotary control, planar with respect to said bottom surface, located at the forward edge of said raised center portion of said chestpiece, said rotary control being capable of controlling the volume of said stethoscope.

11. An ergonometric chestpiece as in claim 10 wherein said plurality of controls includes a first control being capable of controlling power to said stethoscope and capable of controlling the frequency response of said stethoscope.

12. An ergonometric chestpiece as in claim 1 wherein the indented gripping surfaces have a roughened texture.

13. An ergonometric chestpiece as in claim 12 wherein the indented gripping surfaces have a regularly scored surface.

14. An ergonometric chestpiece as in claim 1 further including at least one finger recess located on said top surface of said chestpiece.

15. An ergonometric chestpiece as in claim 14 wherein the finger recess is located on a front portion of the top surface of said chestpiece.

* * * * *